United States Patent [19]
Forschner et al.

[11] Patent Number: 5,095,166

[45] Date of Patent: * Mar. 10, 1992

[54] PROCESS FOR CRACKING PARAFFINS TO OLEFINS

[75] Inventors: Thomas C. Forschner, Richmond; Thomas F. Brownscombe, Houston, both of Tex.

[73] Assignee: Shell Oil Company, Houston, Tex.

[*] Notice: The portion of the term of this patent subsequent to Mar. 3, 2009 has been disclaimed.

[21] Appl. No.: 576,238

[22] Filed: Aug. 31, 1990

[51] Int. Cl.$^5$ .................................................. C07C 4/06
[52] U.S. Cl. ...................................... 585/653; 585/418
[58] Field of Search ................ 585/648, 651, 653, 418

[56] References Cited

U.S. PATENT DOCUMENTS

| | | | |
|---|---|---|---|
| 2,950,240 | 8/1960 | Weisz | 585/324 |
| 3,644,557 | 2/1972 | Senes | 585/651 |
| 3,765,851 | 10/1973 | White | 585/651 |
| 3,839,485 | 10/1974 | Wrisberg et al. | 585/651 |
| 3,872,179 | 3/1975 | Andersen et al. | 585/651 |
| 4,251,348 | 2/1981 | O'Rear et al. | 585/324 |
| 4,255,605 | 3/1981 | Dixon | 585/324 |
| 4,621,162 | 11/1986 | Delzer et al. | 585/651 |
| 4,929,791 | 5/1990 | Laeding | 585/648 |

FOREIGN PATENT DOCUMENTS 0627157 10/1978 U.S.S.R. .............................. 585/651

Primary Examiner—Anthony McFarlane
Attorney, Agent, or Firm—Y. Grace Tsang

[57] ABSTRACT

This invention is a process for the catalytic cracking of paraffins to produce linear olefins while minimizing production of aromatics and branched olefins. The catalyst used is an alkali(ne-erath) metal oxide, optionally supported on a porous oxidic carrier.

14 Claims, No Drawings

PROCESS FOR CRACKING PARAFFINS TO OLEFINS

FIELD OF THE INVENTION

This invention relates to a process for the catalytic cracking of paraffins to olefins, particularly straight chain paraffins to straight chain olefins.

BACKGROUND OF THE INVENTION

Olefins, especially linear olefins, serve as feedstocks for the chemical industry. They can be converted to corresponding alcohols or aldehydes. Higher molecular weight alcohols can further be ethoxylated with ethylene oxide or propylene oxide in the presence of a catalyst to form conventional detergents while lower molecular weight alcohols can be esterified with aromatic acids to form plasticizers. An economically viable process for producing olefins, especially linear olefins with three to thirty carbon atoms, preferably six to twenty carbon atoms, by cracking and dehydrogenating paraffinic feedstock is therefore of substantial commercial interest.

U.S. Pat. No. 3,592,867, patented July 13, 1971, discloses a two-step process for producing ethylene which involves, in a first step, dehydrogenating propane to propylene using a non-acidic, Group VIII noble metal catalyst; and in a subsequent second step, cracking of the resulted propylene with a Group VIII metal component hydrocracking catalyst containing nickel or rhodium.

U.S. Pat. No. 3,725,495, issued Apr. 3, 1973, discloses a process for catalytic cracking, in the presence of steam, of paraffins to produce olefins over a catalyst containing 50-80 wt. % of zirconium and/or hafnium, 5-40 wt. % of oxide of chromium, manganese and/or iron, and 0.1-10 wt % of a compound of an alkali metal and or an alkaline earth metal. When naphtha was cracked by this process, ethylene, propylene and butylenes are produced.

European patent application 219,272, published Apr. 22, 1987, disclosed a process for ethylene production from propane over a ZSM-23 zeolitic catalyst.

European patent application 219,271, published Apr. 22, 1987, disclosed a process for ethylene production from propane over a ZSM-5 zeolitic catalyst.

All of these processes require the use of either transition metals or zeolites as catalysts which are relatively expensive. The expense for catalyst is one of the major costs in a catalytic cracking process. Moreover, the use of conventional zeolites as catalysts for the cracking of paraffinic feedstocks quite often produce a variety of products: olefins, both branched and straight chain, aromatics, paraffins and other products resulting from dealkylation, aromatic side-chain scission, isomerization, condensation and disproportionation reactions. An economically viable process which would crack and dehydrogenate paraffinic feedstock in a single step using a less costly catalyst that would produce only linear olefins, preferably linear olefins with primarily $C_6$ to $C_{30}$, in substantial quantities would be of commercial significance, since the olefins can be used as feedstocks to produce higher valued end products.

SUMMARY OF THE INVENTION

This invention relates to a process for the catalytic cracking of straight chain paraffins to produce straight chain olefins which comprises contacting said paraffins with a catalyst comprising (1) an oxide of alkali or alkaline earth metal optionally dispersed on a refractory and porous carrier, or (2) an alkali metal or alkaline earth metal compound, optionally dispersed on a refractory and porous carrier, which converts at least in part into an oxide of alkali(ne-earth) metal upon calcination, and which compound has been calcined at an elevated temperature. The product of this process contains only small amounts of aromatics and branched olefins.

DETAILED DESCRIPTION OF THE INVENTION

Catalytic Cracking Process

This instant invention provides a catalytic cracking process for converting normal paraffins, that is, straight chain aliphatic hydrocarbons to normal, that is, straight chain olefins. Useful paraffins for the instant process range from $C_4$ to $C_{30}$ and above. These paraffins may be liquid at room temperature such as the $C_4$–$C_{20}$ group or solid at room temperature such as the $C_{21}$–$C_{30}$ and above group, or mixtures of both groups. The catalytic cracking is carried out in a gas and/or liquid phase at catalytic cracking conditions.

Any suitable reactor can be used for the catalytic cracking process of this invention. For example, a fixed bed of catalyst particles can be used, with paraffin feedstock passing through the catalyst bed at catalytic cracking conditions. Generally in commercial operations it is anticipated that a fluidized-bed catalytic cracking (FCC) reactor (preferably containing one or more risers) or a moving-bed catalytic cracking reactor (e.g., a Thermo or catalytic cracker) is employed, preferably a FCC riser cracking unit. Examples of such FCC cracking units are described in U.S. Pat. Nos. 4,377,470 and 4,424,116. Generally a catalyst regeneration unit (for removal of coke) is combined with the FCC cracking as is shown in the above-cited patents.

Specific operating conditions of the cracking operation depend greatly on the type of feed, the type and dimensions of the cracking reactor and the feed rate. Examples of operating conditions are described in the above-cited patents and in many other publications. In an FCC operation, generally the weight ratio of catalyst to feed ranges from about 2:1 to about 10:1, the contact time between oil feed and catalyst is in the range of about 0.2 to about 2 seconds, and the cracking temperature is in the range of from about 350° C. to about 650° C. Generally steam is added with the oil feed to the FCC reactor so as to aid in the dispersion of the oil as droplets. Generally the weight ratio of steam to oil feed is in the range of from about 0.05:1 to about 0.5:1. Pressures will typically range from about atmospheric to about five atmospheres. For fixed bed reactors temperatures and pressures are similar to those of an FCC reactor with liquid hourly space velocities typically ranging from about 0.1 to 10 hours$^{-1}$. The product of the instant process can be used as such as feedstock for processes requiring olefins or it can be further purified before such use by conventional means such as distillation or fractional crystallization.

One important feature of the instant invention is that the cracking process tends to retain higher olefins. The weight ratio of the sum of the percent by weight of all linear olefins produced with number of carbon more than half of the average number of carbon of the paraffinic feed stock to the sum of the percent by weight of the total linear olefins produced with carbon numbers less than half of the average carbon number of the starting material is greater than one. This feature is illustrated by the following formula:

$$A/B > 1$$

As used herein:
- A is the sum of the percent by weight of all linear olefins produced with carbon numbers more than half of the average carbon numbers of the paraffinic feed stock;
- B is the sum of the percent by weight of all linear olefins produced with carbon numbers less than half of the average carbon number of the paraffinic feed stock.

Another important feature of the instant process is that the converted products of the instant process contain only small amounts of aromatics and branched olefins as compared to that of the control process using the control catalyst (Zeolite Y, sodium form), as demonstrated by the experimental results described in the illustrative embodiment infra. The increase in the branching content of the reaction products is less than 5% by weight (basis total feedstock) and the increase in the aromatic content is less than 10% by weight (basis total feedstock). For instance, if the total branching content of the feedstock is 5%, the reaction products would be less than 10%. If the total aromatic content of the feedstock is 5%, the total aromatic content of the reaction products would be less than 15%.

The Cracking Catalyst

The catalysts that are utilized in the process are alkali(ne-earth) metal oxides or compounds of alkali(ne-earth) metals which convert, at least in part, upon calcination to alkali(ne-earth) oxides and which have been calcined at elevated temperatures. The alkali(ne-earth) metal oxides or compounds of alkali(ne-earth) metals are optionally deposited on porous oxidic carriers. Preferred compounds of alkali(ne-earth) metals are those which contain oxygen and which decompose at least in part upon calcination to produce oxides. When the alkali(ne-earth) metal compound can not be decomposed upon calcination to produce an oxide, it is necessary that the compound either can be oxidized at least in part in an oxygen-containing atmosphere to provide an alkali(ne-earth) metal oxide; or alternatively can be dissolved in a suitable solution, precipitated with a suitable oxyanion and subsequently calcined to decompose at least in part to produce an oxide.

As used herein, the term "oxide" as applied to alkali(ne-earth) metal, refers to inorganic metal compounds which contain alkali(ne-earth) metal bound to oxygen, and the oxygen bound to the alkali(ne-earth) metal is not bound to any other element, except, elements in oxidic carriers when the alkali(ne-earth) metal oxide is dispersed in an oxidic carrier which forms a new compound with the oxidic carrier at the temperature adopted in catalyst preparation. It is understood that when the alkali(ne-earth) metal oxide catalyst utilized in the present invention is dispersed on an oxidic carrier, it can occur in several forms. It may retain its chemical identity, with the carrier only acting as a dispersing agent, it may dissolve in the carrier to give a solid solution, or it may form a new stoichiometric compound with the carrier. The concept of formation of compounds between deposited substance and oxidic carriers is generally described by Pott, et al. in *Preparation of catalysts*, edited by B. Delmon et al. 1976, page 538–557, Elsevier Scientific Publishing Company, Amsterdam. Suitable alkali(ne-earth) oxides include beryllium oxide, magnesium oxide, calcium oxide, strontium oxide, barium oxide, lithium oxide, sodium oxide, potassium oxide, rubidium oxide, and cesium oxide.

It is understood that the term "compound" as applied to alkali(ne-earth) metal refers to the combination of alkali(ne-earth) metal with one or more elements by chemical and/or physical and/or surface bonding, such as ionic and/or covalent and/or coordinate and/or Van Der Waals bonding. Illustrative but non-limiting examples of suitable alkali(ne-earth) metal compounds include, by way of non-limiting examples, carbonates, bicarbonates, hydroxides, nitrates, nitrites, sulfates, hydrogen sulfates, sulfites, dithionates, thiosulfates, alkoxides, carboxylates, sulfonates, oxyhalides, iodates, halides and the like.

The term "oxyanionic" or "oxyanion" refers to a negatively charged moiety containing at least one oxygen atom in combination with another element. An oxyanion is thus an oxygen atom in combination with another element. It is understood that ions do not exist in vacuo, but are found in combination with charge-balancing counter ions.

The term "oxidic" as applied to carrier refers to a carrier wherein an element such as aluminum, silicon, and magnesium is bound to oxygen, and possibly one or more different elements, by surface and/or chemical bonding to provide an oxygen-containing moiety (e.g., Al—O—, Si—O—, Mg—O, etc.). Illustrative but non-limiting examples of suitable porous oxidic carriers are alumina, silica, and silica-alumina, magnesia, keisselguhr, ceramics, and combinations thereof.

The term "salt" as used herein is meant to encompass a single salt as well as mixtures of two or more salts. The term alkali(ne-earth) metal refers to any alkali metal or alkaline-earth metal. The term "alkali metal" is used herein as a descriptor of the elements of Group IA of the Periodic Table of the Elements (Li, Na, K, Rb, Cs). The term "alkaline earth metal" is used herein as a descriptor of the elements of Group IIA of the Periodic Table of the Elements (Be, Mg, Ca, Sr, Ba).

The term "basic" refers to having the characteristic of a base; e.g., when placed in a solution, a basic material will have a pH consistent with a base rather than an acid and, if a catalyst, will catalyze chemical reactions that are catalyzed by bases.

In one embodiment of the present invention, paraffins are cracked and dehydrogenated over a catalyst comprising oxides of alkali(ne-earth) metals, or mixtures thereof, which contain primarily only oxygen and alkali(ne-earth) metals, and are substantially free of other elements. In a specific aspect of this embodiment, the oxides are dispersed in a porous oxidic carrier, such as alumina, silica, silica-alumina, keiselguhr, magnesia, other ceramics and the like, or mixtures thereof. Preferably, the oxides, either with or without supporting carriers are calcined prior to the commencement of the catalytic cracking step. Alternatively, they can be used without the calcination step. When a carrier is used, the alkali(ne-earth) metal oxide may retain its chemical identity, with the carrier only acting as a dispersing agent, it may dissolve in the carrier to give a solid solution, or it may form a new stoichiometric compound with the carrier upon calcination.

In another embodiment of the present invention, compounds of alkali(ne-earth) metals which contain oxygen and which decompose at least in part upon calcination to produce alkali(ne-earth) metal oxides are utilized. Illustrative but non-limiting examples include carbonates, carboxylates, nitrates, hydroxides, sulfates, etc. Decomposition can be indicated by the evolution of gases such as carbon oxides, nitrogen oxides, sulfur oxides, water, etc. Decomposition will also be indicated by disappearance at least in part of the particular anionic form associated with the alkali(ne-earth) metal. For example, when carboxylates and alkoxides are calcined, the carboxylate and alkoxide moiety associated with the alkali(ne-earth) metal will decompose giving off carbon oxides and/or water and/or hydrocarbons, thereby disappearing at least in part. Particularly preferred compounds to be used as the catalyst in the present invention are (alkali) carbonates, nitrates and carboxylates. The oxygen-containing alkali(ne-earth) metal compounds may also be supported on a porous oxidic carrier as described above and it may or may not form a new stoichiometric compound with the carrier upon calcination.

In still another embodiment of the present invention, an alkali(ne-earth) metal compound, either supported or unsupported, and which can be oxidized to an oxide upon calcination is employed. Illustrative but non-limiting examples of suitable alkali(ne-earth) compounds include metals, alloys, amalgams, hydrides, amides, sulfides, polysulfides, carbides, naphthlides, salts of cyclopentadiene, and any other materials which would be apparent to one skilled in the art. The alkali(ne-earth) compound is oxidized at least in part upon calcination to provide alkali(ne-earth) metal oxide, which if not supported, may subsequently be deposited on a suitable carrier.

Another method that can be used to prepare the cracking catalyst utilized in the instant process involves the use of an alkali(ne-earth) metal compound precursor, which may or may not be adapted to be decomposable to an oxide upon calcination, which can be dissolved in a suitable solution, precipitated with a suitable oxyanion and can subsequently be calcined to decompose at least in part to produce an oxide. Suitable alkali(ne-earth) metal compound precursors include any salts of alkali(ne-earth) metal soluble in a suitable solution containing suitable oxyanions. Suitable salts include, by way of illustrative non-limiting examples, cyanides, halides, sulfides, thiocyanates, isocyanides, cyclopentadienes, naphthalides, etc. Suitable oxyanions include those which would form insoluble compounds with the alkali(ne-earth) metal salt utilized in a suitable solvent. Illustrative non-limiting examples of suitable oxyanions include hydroxides, carbonates, nitrates, carboxylates, sulfonates, etc. Solvents useful as precipitating media can be inorganic solvents and organic solvents. Illustrative non-limiting suitable solvents include water, alcohols particularly the lower alcohol, hydrocarbons such as hexane, etc. It is understood that not all solvents work well with all salts. One skilled in the art would readily understand that each salt would have its most suitable solvents. Solubility of these salts can be found in Handbook of Chemistry and Physics. The precipitated salt of alkali(ne-earth) metal and oxyanions can be isolated and subsequently calcined to produce oxide. It may also be dispersed in the suitable aforementioned oxidic carrier either prior to or subsequent to calcination.

Mixtures of alkali(ne-earth) metal compounds, as non-limiting examples, two or more salts with different anions, different cations or different anions and cations can be utilized to prepare the cracking catalyst.

The oxidic porous carriers can be combined with the alkali(ne-earth) metal catalysts as a hydrous sol or gel, as an anhydrous activated gel, a spray dried powder or a calcined powder. In one modification, a sol or solution of the carrier can be precipitated to form a gel in the presence of the catalysts utilized in the instant process. When less hydrous forms of the carriers are combined with the instant catalysts, essentially any method of effecting intimate admixture of the components may be utilized, by way of non-limiting examples, mechanical mixing, e.g. mulling, impregnation with suitable solvents, impregnation with molten compound, impregnation by sublimation of the suitable compounds. The impregnation and calcination can be carried out in one continuous step or sequence. The alkali(ne-earth) metal nitrates and carboxylates are particularly suitable for use in the molten impregnation method.

When the method of sublimation is utilized to deposit the alkali(ne-earth) metal compounds, a suitable compound is sublimed at above its sublimation temperature to produce a vaporous salt and the resulting vapor is contacted with the carrier maintained at a temperature near or below the sublimation temperature of the compound thereby causing the vapor to condense upon and within the pores of the carrier thereby impregnating it. Calcination follows to prepare the catalysts utilized in the instant process. Drying before calcination is not required in this case, but may be utilized to remove residual water in the carrier. The impregnation and calcination can be carried out in one continuous step or sequence.

In the solution impregnation method, solutions of alkali(ne-earth) metal salts are used to impregnate the carrier. The solvents utilized to dissolve the salts may be organic or inorganic. The only requirement is that the desired salt be soluble in the particular solvent. Hydroxylic solvents are preferred. Water is a particularly preferred solvent. Organic solvents are particularly useful as solvents for alkali(ne-earth) metal salts which have organic ionic components such as carboxylate, sulfonate, alkoxide, etc. Illustrative, but non-limiting examples of organic solvents include alcohols, including polyhydric alcohols, ethers, esters, ketones, amides, sulfoxides and chloro/fluorohydrocarbons such as the various freons. Specific illustrative examples include methanol, ethanol, glycol, dimethyl ether, methyl acetate, methylethyl ketone, dimethyl formamide ("DMF"), dimethyl sulfoxide ("DMSO"), N-methyl pyrrolidone ("NMP"), hexamethylphosphoramide ("HMPA"), dichlorodifluoromethane, methyl chloride, ethylene dichloride, ethylene carbonate, etc. Illustrative, but non-limiting examples of inorganic solvents include water, liquid ammonia, liquid carbon dioxide, liquid sulfur dioxide, carbon disulfide, carbon tetrachloride, etc. Mixtures of solvents which are mutually miscible may be utilized.

Single or multiple impregnations may be used. When multiple impregnations are used intermediate drying steps, optionally followed by precipitation and/or calcination may be utilized. The drying atmosphere may be neutral, oxidizing, reducing or a vacuum.

The alkalin(ne-earth) metal oxides or compounds, either supported or unsupported, are optionally calcined to eliminate any water, or to be oxidized/decomposed at least in part to produce oxides. Calcination conditions will range from about 150° C. to about 850°

C., preferably from about 200° C. to about 750° C., and more preferably from about 550° C. to about 600° C. Calcining times are dependent on the calcining conditions selected and typically range from about one minute to about twenty hours, although longer or shorter times can be utilized. Calcining conditions and times are also adjusted according to the thermal stability. Calcining atmospheres may be neutral, oxidizing or reducing.

When using an impregnation or an impregnatin/-precipitating solution, the drying and calcining steps may be combined into one integrated process step. Calcining (and drying) can be carried out in situ during the operation of a catalytic process in a catalytic reactor.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The following illustrative embodiments are provided for illustration and are not to be construed as limiting the invention.

ILLUSTRATIVE EMBODIMENT

I. Cracking Catalyst Preparation

Following are illustrative examples of cracking catalysts used in the instant process:

Magnesium Oxide: Magnesium oxide, 98% was purchased from Aldrich and used as received.

Calcium Oxide: Calcium oxide, 98%, was purchased from Aldrich and used as received.

Preparation of Calcium Oxide on Alumina: Alumina, A-201 LaRoche, was ground and sieved to 12-30 mesh. A 50 gram portion of the sieved alumina was then impregnated with 8.44 grams (0.0533 moles) of calcium acetate dissolved in 33.0 ml of water. The catalyst was then dried over night under vacuum at 150° C.

Preparation of Potassium Carbonate on Alumina: Alumina, A-201 LaRoche, was ground and sieved to 12-30 mesh. A 50.7 grams sample of the sieved material was impregnated with 7.1 grams of anhydrous potassium carbonate dissolved in 37.3 ml of water. The catalyst was then dried under vacuum for 2 hours at 150° C.

Preparation of Calcium Oxide/Potassium Carbonate on Alumina: A 50 grams sample of Potassium Carbonate on Alumina, described above, was impregnated with 8.44 grams (0.0533 moles) of calcium acetate dissolved in 33.0 ml of water. The catalyst was then dried over night under vacuum at 150° C.

The following catalyst was used as a control:

Na/Y (Zeolite Y, sodium form) LZ-Y52 zeolite was purchased from Union Carbide Corporation and used as received.

II. Catalytic Cracking Experiments

Catalytic cracking experiments were carried out in a stainless steel flow reactor (34 cm by 1.2 cm internal diameter). The feed was metered into the flow reactor by the use of a Beckman model 110B pump. The nitrogen delivery rates were controlled by the use of regulators and the flow rates were measured with a wet test meter. The reaction products were first cooled with a water condenser as they exited the reactor and then were further condensed by the use of two cold traps operating at −75° C. In a typical experiment 20 milliliters of catalyst was loaded over a 10 millimeter bed of silicon carbide in the flow reactor. A second 10 millimeter silicon bed was placed on top of the catalyst bed to preheat the feed before it contacted the catalyst.

The catalysts were activated by calcination under a nitrogen purge of 50 liters per hour at 575° C. for at least one hour. After calcination the nitrogen flow rate was lowered to 22 liters per hour and the reactor was allowed to cool to the reaction temperature. Hexadecane feed was then pumped into the reactor at a rate of 2.5 liters per liter of catalyst per hour. The contents of the two traps were mixed and analyzed by GC and GC mass spectrometry. The results indicated that more than 50% of the linear olefins produced have more than 8 carbon atoms. The analytical results are presented in Table 1.

As demonstrated from the experimental results, the products of the instant process contains only small amounts of aromatics and branched olefins as compared to that of the control process using the control catalyst Na/Y.

TABLE 1

| CATALYST | Temp | Catalytic Cracking | | | | | A/B > 1[a] |
|---|---|---|---|---|---|---|---|
| | | Conv | LAO | LIO | BIO | PAR | AROM | |
| Na/Y(control) | 550° C. | 61 | 12.5 | 17.6 | 8.0 | 30.0 | 31.9 | no |
| CaO | 550° C. | 15 | 36.4 | 44.7 | <1.0 | 6.3 | <1.0 | yes |
| MgO | 550° C. | 26 | 21.6 | 63.8 | <1.0 | 10.8 | 2.8 | yes |
| CaO on alumina | 550° C. | 13 | 23.5 | 69.4 | <1.0 | 4.2 | 1.9 | yes |
| $K_2CO_3$ on Alumina | 550° C. | 11 | 18.3 | 42.0 | 2.1 | 29.7 | 7.8 | yes |
| CaO and $K_2CO_3$ on Alumina | 550° C. | 21 | 36.2 | 44.7 | <1.0 | 9.8 | 2.9 | yes |

Note:
Conversions and selectivities are in weight percents.
LAO = Linear Alpha Olefins
LIO = Linear Internal Olefins
BIO = Branched Internal Olefins
PAR = Paraffins - excluding hexadecane feed
AROM = Aromatics
[a]A is the sum of the percentage by weight of all linear olefins produced with carbon numbers more than half of the average carbon number of the paraffinic feed stock;
B is the sum of the percentage by weight of all linear olefins produced with carbon numbers less than half of the average carbon number of the paraffinic feed stock;
A/B > 1 indicates the cracking process tends to retain higher olefins.

What is claimed is:

1. A process for catalytic cracking of paraffins which comprises contacting at a temperature ranging from about 350° C. to about 650° C. said paraffins with a catalyst consisting essentially of a composition, or a mixtures thereof, selected from the group consisting of:
- (a) an unsupported oxide of an alkaline earth metal or a mixture consisting of an unsupported oxide of an alkaline earth metal and an unsupported oxide of an alkali metal; and
- (b) an oxide of an alkaline earth metal or a mixture consisting of an oxide of an alkaline earth metal and an oxide of an alkali metal on an oxidic carrier selected from the group consisting of (i) alumina, (ii) silica, (iii) silica-alumina, (iv) magnesia, (v) Keiselguhr and mixtures thereof.

2. The process as claimed in claim 1, wherein said catalyst has been activated by calcination at a temperature from about 150° C. to about 850° C. for at least 1 minute before the commencement of the catalytic cracking process.

3. The process as claimed in claim 1, wherein said catalyst is activated by calcination at a temperature from about 550° C. to about 600° C. for at least about an hour before the commencement of the catalytic cracking process.

4. A process for catalytic cracking of paraffins which comprises contacting at a temperature ranging from about 350° C to about 650° C. said paraffins with a catalyst consisting essentially of a composition, or a mixtures thereof, selected from the group consisting of:
- (a) an unsupported compound of an alkaline earth metal or a mixture consisting of an unsupported compound of alkaline earth metal and an unsupported compound of alkali metal which decomposes at least in part upon calcination to provide an unsupported oxide of an alkaline earth metal or an unsupported mixture consisting of an alkaline earth metal and an alkali metal; and
- (b) a compound of an alkaline earth metal or a mixture consisting of a compound of an alkaline earth metal and a compound of an alkali metal which decomposes at least in part upon calcination to provide an oxide compound of an alkaline earth metal or a mixture consisting of an oxide compound of an alkaline earth metal and an oxide compound of an alkali metal, which compound or mixture is dispersed on a carrier selected from the group consisting of (i) alumina, (ii) silica, and (iii) silica-alumina, (iv) magnesia, (v) Keiselguhr and mixtures thereof; and wherein, the compound of the alkaline earth metal or the mixture comprising the compound of the alkaline earth metal and the compound of the alkali metal is calcined to cause the formation of oxides prior to the commencement of the catalytic cracking process.

5. The process as claimed in claim 4, wherein the calcination is conducted at from about 150° C. to about 850° C. for at least one minute.

6. A process for catalytic cracking of paraffins which comprises contacting at a temperature ranging from about 350° C. to about 650° C. said paraffins with a catalyst prepared by oxidation at least in part, upon calcination in an oxygen-containing atmosphere, of a composition, or a mixture thereof, consisting essentially of:
- (a) an unsupported compound of an alkaline earth metal or a mixture consisting of an unsupported compound of an alkaline earth metal and an unsupported compound of an alkali metal which oxidizes at least in part upon calcination to provide an unsupported oxide of an alkaline earth metal or an unsupported mixture consisting of an oxide of an alkaline earth metal and an oxide of an alkali metal; and
- (b) a compound of an alkaline earth metal or a mixture consisting of a compound of an alkaline earth metal and a compound of an alkali metal which oxidizes at least in part upon calcination to provide an oxide compound of alkaline earth metal or a mixture consisting of an oxide compound of an alkaline earth metal and an oxide compound of an alkali metal, which compound or mixture is dispersed on a carrier selected from the group consisting of (i) alumina, (ii) silica, and (iii) silica-alumina, (iv) magnesia, (v) Keiselguhr, and mixtures thereof.

7. The process as claimed in claim 6, wherein said calcination process is conducted at a temperature ranging from about 150° C. to about 850° C. for at least one minute.

8. The process as claimed in claim 4, wherein said alkali metal compound or alkaline earth metal compound in (a) or (b) is prepared by a process comprising precipitating a solution comprising an alkali metal or an alkaline earth metal compound with an oxyanion.

9. The process as claimed in claim 1, wherein there is less than 5% by weight (basis total feedback) increase in the branching content in reaction products produced by the cracking process.

10. The process as claimed in claim 9, wherein there is less than 10% by weight (basis total feedstock) increase in the content of aromatics in the reaction products produced by the cracking process.

11. The process as claimed in claim 1, wherein the ratio of the sum of the percent by weight of all linear olefins produced with carbon numbers more than half of the average carbon number of the paraffinic feed stock to the sum of the percent by weight of the total linear olefins produced with carbon numbers less than half of the average carbon number of the paraffinic feed stock is greater than one.

12. The process of claim 1, wherein the paraffins have 10 to 40 carbon atoms, wherein more than 50% of the linear olefins produced have more than five carbon atoms.

13. A process for catalytic cracking of paraffins of 12–40 carbon atoms which process comprises contacting at a temperature ranging from about 350° C. to about 650° C. said paraffins with a catalyst consisting essentially of a composition, or a mixtures thereof, selected from the group consisting of calcium oxide or magnesium oxide which has been calcined at from about 400° C. to about 650° C. before the commencement of the catalytic cracking process, wherein there is less than a 5% by weight (basis total feedstock) increase in branching content of reaction products produced by the cracking process and less than a 10% by weight (basis total feedstock) increase in aromatic content of the reaction products produced by the cracking process, wherein more than 50% of the linear olefins produced have more than five carbon atoms.

14. A process for catalytic cracking of paraffins of 12–40 carbon atoms which process comprises contacting at a temperature ranging from about 350° C. to about 650° C. said paraffins with a catalyst consisting essentially of calcium oxide supported on alumina or magnesium oxide supported on alumina, which catalyst has been calcined at form about 400° C. to about 650° C. before the commencement of the catalytic cracking process; wherein there is less than a 5% by weight (basis total feedstock) increase in branching content of reaction products produced by the cracking process and there is less than 10% by weight increase in the aromatic content of reaction products produced by the cracking process, wherein more than 50% of the linear olefins produced have more than five carbon atoms.

* * * * *